United States Patent
Tazberik et al.

(10) Patent No.: US 10,786,441 B2
(45) Date of Patent: Sep. 29, 2020

(54) SKIN BARRIER REPAIR AND MAINTENANCE COMPOSITION

(71) Applicant: Skinintegra, Inc., Huntington Beach, CA (US)

(72) Inventors: Erika Tazberik, Huntington Beach, CA (US); Christopher M. Marrs, Rancho Palos Verdes, CA (US); I-Ting Wu, Gardena, CA (US)

(73) Assignee: SKININTEGRA, INC., Huntington Beach, CA (US)

( * ) Notice: Subject to any disclaimer, the term of this patent is extended or adjusted under 35 U.S.C. 154(b) by 547 days.

(21) Appl. No.: 15/815,962

(22) Filed: Nov. 17, 2017

(65) Prior Publication Data

US 2018/0140535 A1 May 24, 2018

Related U.S. Application Data

(60) Provisional application No. 62/424,740, filed on Nov. 21, 2016.

(51) Int. Cl.

| | | |
|---|---|---|
| *A61K 36/00* | (2006.01) |
| *A61K 8/92* | (2006.01) |
| *A61K 8/42* | (2006.01) |
| *A61K 8/43* | (2006.01) |
| *A61Q 17/00* | (2006.01) |
| *A61K 8/891* | (2006.01) |
| *A61Q 19/00* | (2006.01) |
| *A61K 8/365* | (2006.01) |
| *A61K 31/202* | (2006.01) |
| *A61K 45/06* | (2006.01) |
| *A61K 31/20* | (2006.01) |
| *A61K 36/47* | (2006.01) |
| *A61K 31/201* | (2006.01) |
| *A61P 17/10* | (2006.01) |
| *A61P 17/02* | (2006.01) |
| *A61K 36/185* | (2006.01) |
| *A61K 31/17* | (2006.01) |

(52) U.S. Cl.
CPC ............. *A61K 8/922* (2013.01); *A61K 8/365* (2013.01); *A61K 8/42* (2013.01); *A61K 8/43* (2013.01); *A61K 8/891* (2013.01); *A61K 31/17* (2013.01); *A61K 31/20* (2013.01); *A61K 31/201* (2013.01); *A61K 31/202* (2013.01); *A61K 36/185* (2013.01); *A61K 36/47* (2013.01); *A61K 45/06* (2013.01); *A61P 17/02* (2018.01); *A61P 17/10* (2018.01); *A61Q 17/00* (2013.01); *A61Q 19/007* (2013.01); *A61K 2800/30* (2013.01)

(58) Field of Classification Search
CPC ........................................................ A61K 36/00
USPC ........................................................ 424/725
See application file for complete search history.

(56) References Cited

U.S. PATENT DOCUMENTS

2015/0258006 A1* 9/2015 Delowsky ................ A61K 8/65
424/70.12

FOREIGN PATENT DOCUMENTS

| WO | 2005107476 A2 | 11/2005 |
| WO | 2010106571 A2 | 9/2010 |
| WO | 2011082151 A1 | 7/2011 |

OTHER PUBLICATIONS

Gold Bond Ultimate http://www.walgreens.com/store/c/gold-bond-diabetic-skin-relief-foot-cream/ID=prod6177516-product—webpage no longer available, please see: https://www.google.com/search?q=gold+bond+ultimate&rlz=1C1CHBF_enUS700US700&oq=gold+bon&aqs=chrome.0.69i59j0j69i57j69i60j0l2.2264j0j9&sourceid=chrome&ie=UTF-8.

Eucerin DB Cream http://www.amazon.com/Eucerin-Diabetics-Relief-Creme-Ounce/dp/B00Q2MYUFG.

* cited by examiner

*Primary Examiner* — Michael V Meller
(74) *Attorney, Agent, or Firm* — Meagher Emaneul Laks Goldberg & Liao, LLP

(57) ABSTRACT

A composition of matter and method for treating compromised skin is disclosed, providing improved skin barrier repair and maintenance properties. The composition of matter comprises at least one lipid selected from a group consisting of lipids defined by a predetermined lipid profile and at least one skin nutrient selected from a group consisting of nutrients defined by a predetermined nutrient profile, but is substantially free of petrolatum. This composition of matter produced a surprising improvement when applied to cracked skin of, e.g., diabetes mellitus patients or other individuals with dry or damaged skin.

5 Claims, 4 Drawing Sheets

| |
|---|
| GOLD BOND® Ultimate Diabetic Skin Relief Skin Protectant Foot Cream |
| Dimethicone |
| White Petrolatum |
| Water |
| Glycein |
| Glyceryl stearate |
| Distearyldimonium chloride |
| Aloe barbadensis leaf juice |
| Polyethylene |
| Stearyl alcohol |
| Cetearyl alcohol |
| Methyl gluceth-20 |
| Behentrimonium methosulfate |
| Steareth-21 |
| Steareth-2 |
| Allantoin |
| Cocodimonium hydroxypropyl hydrolyzed Rice protein |
| Cetyl alcohol |
| Tocopheryl acetate |
| Butyrospermum parkii (shea) butter extract |
| PEG-10 rapeseed sterol |
| Polysorbate 60 |
| Ceramide 2 |
| Hydrolyzed collagen |
| Stearamidopropyl PG-dimonium chloride Phosphate |
| Jojoba esters |
| DMDM hydantoin |
| Magnesium ascorbyl phosphate |
| Butylene glycol |
| Methylparaben |
| Palmitoyl oligopeptide |
| Propylene glycol |
| Hydrolyzed jojoba esters |
| Propylparaben |
| EDTA |
| Potassium hydroxide |
| Tribehenin |
| C12-15 alkyl benzoate |
| Retinyl palmitate (309-007) |

FIG. 2A

| EUCERIN® Diabetic Dry Skin Relief Foot Cream |
|---|
| Water |
| Glycerin |
| Urea |
| Cetearyl Alcohol |
| Sodium Lactate |
| Petrolatum |
| Caprylic/Capric Triglyceride |
| Hydrogenated Coco-Glycerides |
| Octyldodecanol |
| Ethylhexyl Cocoate |
| Dimethicone |
| Aluminum Starch Octenylsuccinate |
| Sorbitan Stearate |
| Lactic Acid |
| Phenoxyethanol |
| PEG-40 Castor Oil |
| Carbomer |
| Sodium Cetearyl Sulfate |

FIG. 2B

| EUCERIN® |
| --- |
| Intensive Repair Extra Enriched Foot Cream |
| Water |
| Glycerin |
| Urea |
| Cetearyl Alcohol |
| Sodium Lactate |
| Caprylic/Capric Triglyceride |
| Petrolatum |
| Ethylhexyl Cocoate |
| Hydrogenated Coco-Glycerides |
| Octyldodecanol |
| Aluminum Starch Octenylsuccinate |
| Dimethicone |
| Sorbitan Stearate |
| Peg-40 Castor Oil |
| Sodium Cetearyl Sulfate |
| Carbomer |
| Lactic Acid |
| Phenoxyethanol |

FIG. 2C

SKIN BARRIER REPAIR AND MAINTENANCE COMPOSITION

CROSS-REFERENCE TO PRIOR FILED APPLICATIONS

This application claims the benefit of U.S. Provisional Application No. 62/424,740 filed Nov. 21, 2016.

BACKGROUND OF THE INVENTION

Skin pathologies are a common complication of wounds, especially those related to diseases such as diabetes. Diabetes, for example, causes nerves that control the oil and moisture in a person's foot to stop functioning, which can cause changes in the skin of the foot. At times that skin may become very dry, and may peel and crack. Patients with diabetes exhibit dryer, thinner skin with a flakier outer layer, and they are more exposed to skin infections caused by both bacterial and fungal sources. Moreover, skin elasticity is compromised in diabetic patients similarly to skin in elderly patients, thus, having a higher tendency to break and injure.

In addition, after a wound site stops bleeding, the human body triggers white blood cells to protect the affected area from infection, guarding against potentially harmful bacteria and viruses. When inflammation occurs in the body, chemicals are expelled from the white blood cells into the wound site, causing redness and warmth. But while inflammation protects the wound site against wound infection, inflammation can also cause insulin resistance and lead to diabetes complications.

Doctors often suggest patients with diabetes use moisturizing creams and lotions to prevent drying of the skin, or provide artificial barrier functionality through the use of occlusive materials. While it has been suggested that Omega-3 and Omega-6 oils may be useful for the skin or eyes, prior art does not appear to suggest a topical combination in compositions free of petrolatum, particularly to treat diabetic skin and/or visibly cracked skin on the feet.

For example, WO 2011082151 A1 (Warren, et al.) teaches a wipe for treating diaper rash, the wipe comprises a substrate and a stable oil material, where the oil material comprises an Omega-6 fatty acid having an OSI of at least about 10 hours. However, it does not teach the use of urea, and indicates the use of water-based ingredients at all leads to undesirable instability.

WO 2005107476 A2 (Heeg, et al.) teaches an ingestible nutraceutical comprising cranberry seed oil, which may also include high doses of Omega-3/6 fatty acids, but only teaches a "scrub, cleanser, soap, or spa product" comprising cranberry seed oil.

WO 2010106571 A2 (Aleo, et al.) discloses a composition for use in the eyes, the composition having a ratio of Omega-3 to Omega-6 fatty acids that may range from 20:1 to 1:20, and in preferred compositions the weight ratio of (EPA+DHA) to GLA is comprised between 4:1 and 1:4.

However, to date, these lotions and creams cannot provide sufficiently rapid relief from dry or cracked skin and relief from inflammation. These topical lotions and creams sometimes require 2 weeks or more to see results.

As such, there remains a need for a topically applied composition that provides rapid relief from dry, cracked and injured skin and relief from inflammation, especially in diabetic patients, or in wound care (e.g., wound dressing). Further, it would be beneficial for such a topically applied composition to have other applications, including inflammatory acne, keratosis, eczema, psoriasis, cuts and wound, cyst, post-surgery recovering with and without stitches, and in non-human applications, such as in pet care applications.

BRIEF SUMMARY OF THE INVENTION

The present invention is directed to a composition of matter with the ability to enhance skin's natural repair and maintenance functions. In the present invention, compositions and methods are provided that utilize lipids and nutrients chosen based on skin lipid and nutrient profiles, but do not contain petrolatum. Among the many different possibilities contemplated, the composition of matter may also advantageously contain urea, a humectant, or dimethicone, and the lipids utilized may involve Omega-3 and Omega-6 fatty acid oils, which may by natural extracts such as sacha inchi oil or sea buckthorn oil, at ratios between 1:3 and 3:1 by weight. The compositions may advantageously also comprise other skin lipid mimicking oils, and may also include aminoguanidine bicarbonate, a salt of aminoguanidine bicarbonate, lactic acid, or a salt of lactic acid, one or more vitamins, one or more minerals, and/or one or more antioxidants. The skin profiles may also advantageously be from a single subject or selected from a predefined set of profiles. The method involves application of the composition of matter to at least a portion of compromised skin, leaving the composition on the skin, and reapplying at least once a day, and preferably at least twice a day, for a day, a week, a month, several months, or even longer depending on the nature of the injury or condition.

BRIEF DESCRIPTION OF DRAWINGS

FIGS. 2A, 2B, and 2C are ingredient list of comparative formulations.

DETAILED DESCRIPTION OF THE INVENTION

Figure 1:
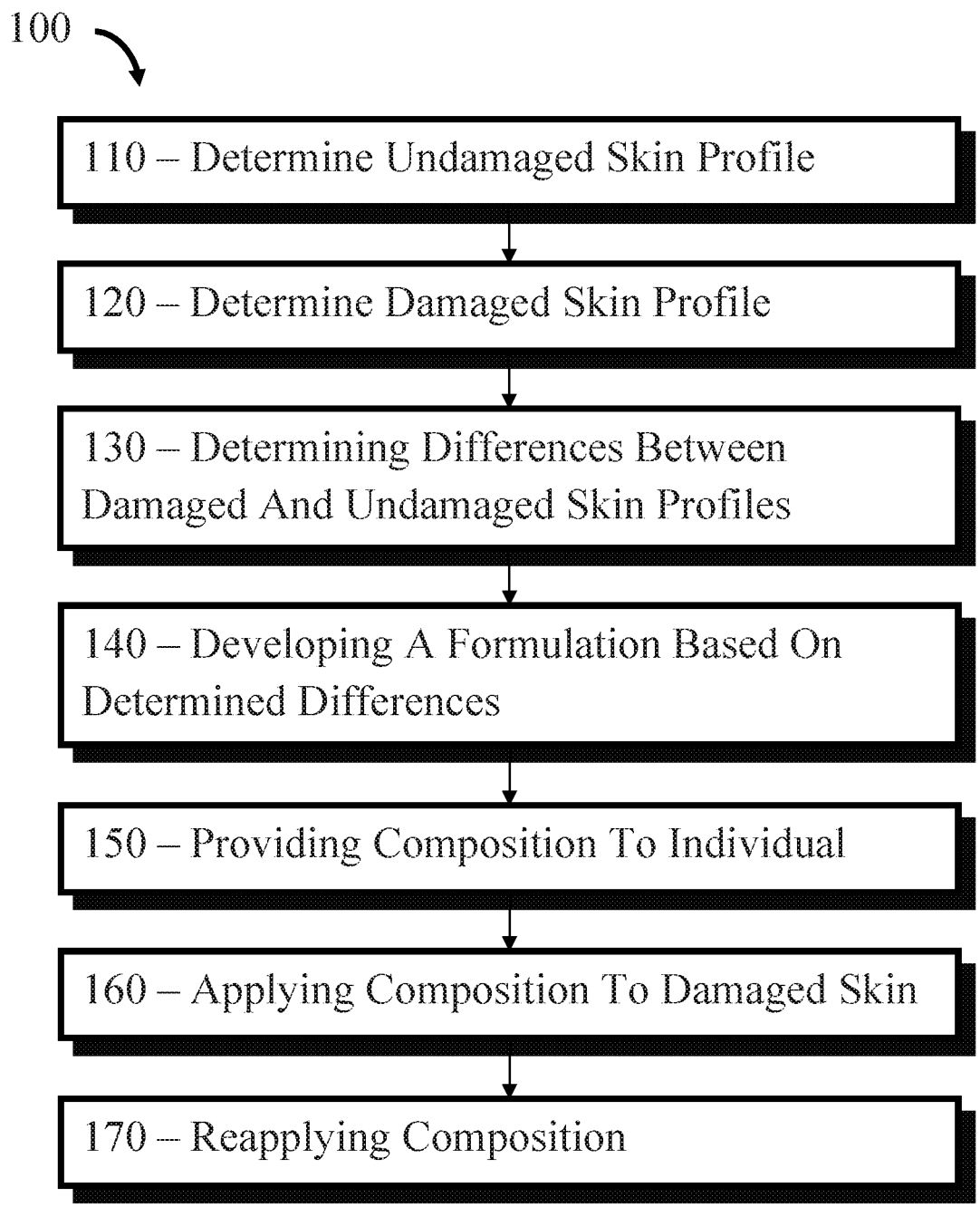
FIG. 1 is a flowchart describing one embodiment of the present invention.

As used herein, any percentage used in reference to a composition is intended to be a design specification for the composition. As is known, there is variation in the manufacturing process, and that variation will depend on a number of site, process, and test method-specific factors. The allowable variation of "active" ingredients also varies, and the actual composition of these ingredients as they may appear in commercial use may vary from the design specification by, for example, as much as 30%, more preferably as much as 20%, and most preferably as much as 10%.

The term "lipid profile," as used herein, is a defined composition of skin lipids. This profile is typically generated via a composite of measurements of multiple individuals' skins, although other approaches, including but not limited to measurements of a single individual's skin, or basing the profile on a general skin lipid composition profile, may be utilized. In preferred embodiments, the lipid profile is a profile of lipids in at least the epidermis and dermis.

The term "nutrient profile," as used herein, is a defined composition of skin nutrients. This profile is typically generated via a composite of measurements of multiple individuals' skins, although other approaches, including but not limited to measurements of a single individual's skin, may be utilized. Typically, the nutrient profile will include, but is not limited to, a combination of vitamins, minerals, and natural moisturizing factor (NMF). In preferred embodiments, the nutrient profile is a profile of nutrients in at least the epidermis and dermis.

The term "skin profile," as used herein, is a defined composition of skin lipids and nutrients and natural moisturizing factor (NMF), and is a combination of the "lipid profile" and "nutrient profile." This profile is typically generated via a composite of measurements of multiple individuals' skins, although other approaches, including but not limited to measurements of a single individual's skin, may be utilized Every individual's undamaged skin has a unique lipid profile and nutrient profile that is required in order to provide all the various skin functions (e.g., preventing loss of essential body fluids and penetration of toxic substances). The primary sources of the human epidermal lipidome are the sebum and the cells of the stratum corneum (SC). SC-derived lipids are typically primarily composed of about between about 30% and about 50% ceramides, with the remainder made up of up to about 35% cholesterol and up to about 35% free fatty acids, while sebum lipids tend to be primarily composed of Triglycerides, free fatty acids, wax esters, squalene, cholesterol esters, and cholesterol. However, the majority of the epidermal surface lipids are of sebaceous origin as compared to the lipids produced by the epidermis, especially in areas with the highest concentrations of sebaceous glands (e.g., forehead), where the epidermal origin lipids can average between, e.g., 5 to 10 micrograms per square centimeter, compared with average sebum recoveries of 150 to 300 micrograms per square centimeter. Thus, an individual's lipid profile is typically driven by the composition of the sebum lipids. As an example, in extremities, the sebum levels are typically very minimal.

The lipid profile in dry or damaged skin differs from the profile in undamaged skin, and specifically in diabetics. Damage to the epidermis appears to cause the sebaceous glands beneath the wound to cease producing lipid.

Similarly, the skin also has a nutrient profile—a range of vitamins and minerals and antioxidants present in the skin, such as vitamins A, C, and E, as well as iodine, zinc, potassium, and sodium. Typically, these vitamins and minerals are acquired through proper nutrition, and released into the dermis, flowing up into the epidermis. These vitamins and minerals and antioxidants can impact skin health directly and indirectly. For example, Vitamin C directly activates the transcription factors involved in collagen synthesis and stabilizes pro-collagen mRNA that regulates Type I and III collagen synthesis, and vitamin C indirectly decreases collagen degradation by increasing synthesis of the tissue inhibitor of metalloproteinase-1 (TIMP-1), which decreases collagen degradation. Deficiencies in these nutrients therefore reduce skin health and can lead to dry or damaged skin, and impair the skin's ability to repair damage. Further, delayed wound healing appears to be caused in part by deregulation of signaling molecules that mediate the inflammatory response (e.g., anti-inflammatory cytokine [IL-4 and IL-10] and proinflammatory cytokine [IL-1β, IL-6, and TNF-α]), embodiments of the present invention may advantageously have anti-inflammatory as well as pro-inflammatory properties depending on concentration. Other embodiments may utilize one or more mineral complexes, boosting cellular metabolism to promote cell defense. Such mineral complexes may, for example, utilize an alkaline earth metal gluconate or aspartate, and/or a transition metal gluconate or aspartate. In certain embodiments, such complexes may be used to provide, for example, boosting cellular respiration, ATP production and epidermis turnover, preventing, slowing, or reducing the effects of the glycation process, blocking free radicals and/or activating intercellular communication.

The present disclosure is drawn to a composition for skin repair and maintenance, where the composition is designed to modify damaged skin's lipid and nutrient and moisturizing factor profiles to match a predetermined lipid and nutrient and moisturizing profile, by providing missing or compromised lipids and nutrients and moisturizing factor, or derivatives thereof. Preferred embodiments provide for more than merely what is present in the epidermis; for example, providing lipids that mimic the combination of both sebaceous and epidermal lipids. Thus, preferred embodiments comprise lipids, anti-oxidants, and natural moisturizing factor (NMF) designed to provide optimal functionality for compromised/injured skin.

Compositions of the present disclosed approach have surprisingly strong efficacy in reducing the effects of severely dry (e.g., diabetic skin) and in repairing cracks in said skin, particularly on human feet, hands and elbows. Other application areas and skin issues such as acute and chronic wound and trauma injuries like cuts show rapid healing benefits and scar minimization. Compositions of the present disclosed approach include at least one lipid from a predetermined lipid profile, including but not limited to an Omega-3 fatty acid oil and an Omega-6 fatty acid oil in the least altered format—meaning the Omega-3 and Omega-6 oil source contains other essential components such as flavonoid, antioxidants, minerals etc. Compositions also include at least one nutrient from a predetermined nutrient profile, including but not limited to vitamin E, C and/or derivatives thereof. These compositions are substantially free of petrolatum.

NMF materials, such as urea, lactate, amino acids, and pyrrolidone carboxylic acid (PCA), exist in normal skin, and are generally known in the industry. These materials increase skin hydration, skin elasticity, and smoothness, and can stimulate the expression of various enzymes relating to, e.g., ceramide synthesis and barrier formation. Typically, the NMF function by enhancing the water binding capacity in the stratum corneum by exposing water-binding sites on corneocytes, and decreasing transepidermal water loss. Certain NMF, such as urea, may also play a role in metabolism and excretion of nitrogen containing products, and may be able to improve cell differentiation by increasing gene expression of, e.g., transglutaminase, luricrin, and filaggrin, In certain embodiments, a material may be utilized that improves the sloughing off tough, callused skin. For example, urea provides both NMF functionality, and helps with the process of sloughing off skin cells.

In certain embodiments, the formula may also comprise at least one glycosaminoglycan, and preferably a glycosaminoglycan that is present in human skin. This includes, but is not limited to hyaluronic acid, which may be used to attract and retain moisture deep within the skin, as opposed to merely moisturizing the outer layer of the epidermis.

In certain embodiments, the formula may also comprise inhibitors of advanced glycation and/or lipoxidation end products (AGEs/ALEs). Preferred inhibitors include, but are not limited to, ALE inhibitors may include aminoguanadine, which is known to inhibit production of harmful molecules such as advanced glycation end products, induced by increased glucose level In certain embodiments, the at least one lipid is used in combination of other skin lipid mimicking oils. These skin dermal mimicking lipids may be designed to promote healing in dry and cracked skin. The combination of skin dermal mimicking lipids is designed to work on problem skin areas layer-by-layer to provide conditioning, exfoliating and hydrating to soothe and promote healing.

In one embodiment, the weight percentage of total Omega-3 fatty acid oil and the weight percentage of Omega-6 fatty acid oil are in a ratio from about 1:3 to about 3:1, preferably from about 1:2.5 to about 2.5:1, more preferably from about 1:2 to about 2:1, still more preferably from about 1:1.5 to about 1.5:1, and most preferably about 1:1. Other skin-mimicking oils suitable for use with the inventive compositions include, but are not limited to, sesame oil, rice bran oil or jojoba oil, or other compounds capable of mimicking at least a portion of the skin lipids profile. In preferred embodiments, the lipids are comprised of Accelerated Epi-Lipids™ (a blend of oils comprising Omega-3/6 and other oils to profile skin lipids).

These lipids may also provide other benefits. For example, Omega-3, Omega-6, and ceramide may also be utilized to soothe inflammation and increase elasticity of the skin. Other functions include, but are not limited to, barrier repair emollient and lubrication.

In preferred embodiments, compositions of the present disclosed approach include both a "fatty" or "oil" phase, and an aqueous phase. The fatty phase, which typically comprises up to about 30% by weight of the composition, and preferably between about 10% to about 20%, and generally includes at least one Omega-3 rich oil. These oils are non-polar liquid ester of fatty acids. The Omega-3 rich oil is rich in Omega-3 fatty acids such as alpha-linolenic acid. High Omega-3 oils include natural extract such as sea buckthorn oil or sacha inchi oil (also referred to as "Inca peanut," "*Plukenetia volubilis*," or "pracaxi oil"). Certain commercially available versions of Sacha inchi oil may be comprised of about 49% Omega-3 oils.

The fatty phase generally also includes at least one oil that is high in Omega-6 fatty acids such as linoleic acids. A suitable high Omega-6 oil is a natural extract such as sea buckthorn oil (i.e., oils extracted from genus *Hippophae*). Certain commercially available versions of Sea buckthorn oil may be comprised of about 39% Omega-6 oils.

Both sacha inchi and sea buckthorn oil contain some level of both Omega-3 and Omega-6 oils. Sea buckthorn oil, for example, contains some level of both Linolenic acid (Omega-3) and Linoleic acid (Omega-6), and includes Omega-9 and the even less common Omega-7. In certain embodiments, the fatty phase has sufficient natural extract to provide between about 0.1% and about 1% of Omega-3 and/or Omega-6 oil by weight in the composition, and preferably less than about 0.5%.

While certain embodiments do not use dimethicone, in certain other embodiments, the formulation may advantageously comprise dimethicone. Although not limited to such embodiments, some embodiments of these compositions utilize up to about 5% by weight or between 0.9 and 1.1% by weight, inclusive. Other preferred embodiments utilize between about 0.1% and about 1% by weight. Additionally, preferred embodiments are also preservative-free and/or steroid-free. Various embodiments may also be substantially free of materials considered potentially harmful skin irritants, including but not limited to fragrances, dyes, parabens, phthalates, and petrolatum.

The aqueous phase may serve as a vehicle useful for facilitating the spreading of the composition across the skin. The phase preferably comprises water. It may also comprise glycerin. When glycerin is utilized, the formulation generally comprises less than 30% of glycerin, and preferably between 5 and 10% glycerin. In certain embodiments, the aqueous phase also includes one or more of aminoguanidine bicarbonate, lactic acid, or salts thereof.

Table 1 shows formulation target weight percentage ranges for preferred embodiments of skin barrier repair and maintenance compositions.

TABLE 1

| Example Formula #1 | |
|---|---|
| Ingredient | Target Wt % |
| Water | 20-60 |
| Urea | 5-40 |
| Glycerin | 1-20 |
| *Oryza Sativa* (Rice) Bran Oil | 1-20 |
| *Sesamum Indicum* (Sesame) Seed Oil | 1-20 |
| Propanediol | 1-5 |
| *Butyrospermum Parkii* (Shea Butter) Extract | 1-5 |
| Dimethicone | 1-5 |
| Arachidyl alcohol | 0.1-1 |
| Glyceryl Caprylate | 0.1-1 |
| Cetearyl Alcohol | 0.1-1 |
| Lactic acid | 0.1-1 |
| *Hippophae Rhamnoides* Seed Oil | 0.1-1 |
| *Plukenetia volubilis* seed oil | 0.1-1 |
| *Simmondsia Chinensis* (Jojoba) Seed Oil | 0.1-1 |
| Beeswax | 0.1-1 |
| Behenyl alcohol | 0.1-0.5 |
| Xanthan Gum | 0.1-0.5 |
| Arachidylglucoside | 0.1-0.5 |
| Arginine | 0.1-0.5 |
| Aminoguanidine Bicarbonate | 0.1-0.5 |
| Sodium Polyacrylate | 0.1-0.5 |
| Cetearyl Glucoside | 0.1-0.5 |
| Ethylhexyl Stearate | 0.1-0.5 |
| Caprylhydroxamic Acid | 0.1-0.5 |
| Dipotassium Glycyrrhizate | 0.1-0.5 |
| Sodium hyaluronate | 0.1-0.5 |
| Potassium lactate | <0.1 |
| Ascorbyl Isostearate | <0.1 |
| Tocopherol | <0.1 |
| *Trigonella Foenum-Graecum* Seed Extract | <0.1 |
| *Caesalpinia Spinosa* Gum | <0.1 |
| Trideceth-6 | <0.1 |
| Magnesium aspartate | <0.1 |
| Zinc gluconate | <0.1 |
| Ceramide NP | <0.1 |
| Copper gluconate | <0.1 |

Preferred embodiments are oil-in-water emulsions. However, other embodiments, such as water-in-oil emulsions, are also envisioned. Similarly, although a preferred embodiment of the composition is a non-foaming leave-on product, other embodiments are envisioned.

In other preferred embodiments the composition is non-foaming and is not rinsed off such as would be done with a cleansing composition. However, other leave-on and rinse-off compositions are also envisioned.

The delivery method employed by this formula is similar in composition to skin's own epidermal lipids, skin nutrients and natural moisturizing factor. By avoiding the use of a petrolatum occlusive barrier, this formula allows beneficial ingredients to absorb quickly and penetrate deeply into the layers of the skin barrier to deliver repairing actives where they are needed, thereby inducing the skin's own repair mechanism to help promote wound healing. In addition, by mimicking the skin's lipid and nutrient profiles, the formula reduces the risk of triggering an inflammation response. For example, certain embodiments contain a vital composition of nutrients. These compositions are typically gentle to skin and has substantially no negative effect on cell membrane integrity and substantially no effect on cell viability and metabolism when tested in-vitro. Embodiments are typically rich in antioxidants and some are in a form that can penetrate into and protect living human cells from free radical damage. Exemplary antioxidants include Tocopherols, Tocotrienols, Gamma Oryzanol, Phytosterols, Polyphenols and Squalene. These formulations as a whole trigger less inflammatory behavior of human polymorphonuclear (PMN) cells, both under normal culture condition and under inflammatory conditions. Further, the formula shows a significant support of human skin cells in the in-vitro wound healing model by promoting dermal fibroblasts formation. This fibroblasts formation is independent of cell-cell contact with the existing monolayer.

As can be seen by one of skill in the art, the aqueous phase quantity in the Example Formula above represents 30-90% of the formula. The phase includes less than 40% urea. The oil phase may be quite large, some preferred versions utilize oil phases comprising up to 55% of the formula composition, with more preferred versions comprising up to 20% of the formula composition.

Example Manufacturing Process

One example of a manufacturing process for an exemplary skin repair and maintenance composition, such as Example Formulation #1, is described herein. In a first tank, prepare aqueous phase by charging a first tank with water, then adding the thickeners, one at a time, mixing until well dispersed. Add in remaining relatively temperature insensitive aqueous phase ingredients, ensuring each are dispersed before adding the next ingredient. Begin heating the first tank to a temperature above the melting point of the ingredient with the highest melting point. Here, a target of 80 degrees C. may be appropriate. Typically, this temperature will not exceed 85° C.

In a separate tank, prepare an oil phase. Add the oils and oil soluble ingredients, then heat to a temperature above the melting point of the ingredient with the highest melting point. Again, this temperature will typically not exceed 85° C. Typically, this temperature will be the same as the temperature of the aqueous phase.

Add the oil phase to the aqueous phase while mixing the aqueous phase, and then homogenize the combined phases. Cool to approximately room temperature, and add any remaining ingredients. As part of this process, adjust the pH as desired; pH values for topical skin preparations will often range from between 4 and 8.5, although a preferred range is between 4.5 and 6.5. Continue mixing the batch until uniform.

Those in the art will understand that a number of variations may be made in the disclosed embodiments, including known methods for improving process yield, efficiency, vessel capabilities, conversion from batch to continuous processing, etc., all without departing from the scope of the invention, which is defined solely by the appended claims.

Skin Profiles

It is envisioned that any appropriate method of determining a lipid and nutrient profile is acceptable. Various approaches for determining a lipid and nutrient profile are known in the art, including but not limited to tape stripping, followed by extraction (e.g., using an 20:80 ethyl acetate:methanol mixture) and separation via HPLC/HPTLC, or thin-layer chromatography (TLC) combined with matrix-assisted laser desorption/ionization time-of-flight mass spectrometry (MALDI-TOF MS).

In some embodiments, the skin profiles may be personalized for a given formulation that is, an individual may have their own skin profiles analyzed—their damaged skin profile and/or their undamaged skin profile—and an appropriate composition formulated for that individual. Alternatively, formulations may be designed where either or both of the damaged or undamaged skin profiles may be an idealized profile, such as the skin profile of a young male or female otherwise in perfect health. In certain embodiments, multiple profiles may be used, each predetermined such that each profile is designed for a certain category of individual or condition. For example, one profile might be designed for middle-aged females with cracked skin on their feet due to Type II diabetes, while another profile might be for teenage boys with compromised skin due to eczema. Various combinations of these approaches may also be utilized. For example, it is envisioned that a walk-up scanning device could be utilized, whereby a user may, for example, allow a portion of their body to be scanned, after entering in some basic user information (such as age, sex, etc.) as needed, in order for the device to determine which predetermined profile will be the best match for their particular skin condition, and potentially including identifying an appropriate formulation for use by the individual.

It is also envisioned that certain embodiments could be included in a kit for any skin trauma, e.g., in fire trucks or ambulances, in burn centers, trauma centers, and/or for skin cancer treatments, pre- and post-laser and surgical procedures. Kits would typically include the composition of matter, as well as other aspects such as bandages, wipes, etc.

Methodology

One embodiment of an approach to repairing damaged skin is seen in FIG. 1. The method (100) as shown in FIG. 1 begins by determining an undamaged skin profile (110), and then determining the skin profile for damaged skin (120). One of skill in the art will recognize that these steps could also be performed in reverse order, or even substantially simultaneously. While the determination is preferably made by direct testing of a target individual's skin, other approaches are acceptable, including but not limited to utilizing data from experiments performed on or by others to build the necessary profiles. Once the profiles are provided, differences between the damaged and undamaged skin profiles are identified (130). A formulation can then be developed based, in part, on the determined/identified differences (140), including but not limited to reduced levels of one or more lipids or nutrients. A composition can then be manufactured or otherwise produced. The composition can then be provided to a target individual (150), who either applies the composition to himself, herself, or another (including, e.g., pets, domesticated animals, etc.), has it applied to them by someone else, or otherwise causes the composition to be applied (160). In some embodiments, this may be done by, e.g., having the composition applied to a substrate, such as a bandage, or any other wound protective substrate, including e.g., "artificial skin"-type polymers or collagen scaffolds and then applying the substrate with the composition over or onto the damaged skin. The composition is then reapplied (170) as necessary, preferably at least once a day for two or more days, more preferably for 7 or more days for significant improvements. Some chronic skin issues might require longer application times, e.g., from a few weeks to a couple of months.

Skin Trauma After Razor Shaving (STARS) Bioassay

Example Formula #1 was tested using a Trauma Razor Test as an initial assessment of product efficacy in skin barrier repair. Example Formula #1 was compared against a petrolatum/dimethicone formulation (GOLD BOND® Ultimate Diabetic Skin Relief Skin Protectant Foot Cream), and a urea/petrolatum formulation (EUCERIN® Intensive Repair Extra Enriched Foot Cream), the ingredient lists of which are shown in FIGS. 2A-C, respectively.

The STARS bioassay was used to temperately disrupt the integrity of the stratum corneum to assess the ability of topical skincare products to aid in restoring the normal skin barrier function.

Subjects reported to the lab on Day 0 for baseline capacitance measurements, conductance measurements and transepidermal water loss (TEWL) measurements of the four volar forearm test sites. The integrity of the stratum corneum was then challenged by dry shaving of the skin surface of the volar forearms with a disposable razor. The result was significantly elevated transepidermal water loss and eventual erythema associated with razor "chafed" skin.

On Day 1, post-trauma capacitance, conductance and transepidermal water loss (TEWL) measurements were taken from the dry-shaved test sites. The test products were applied to 3 of the 4 dry-shaved sites and the remaining dry-shaved site remained as a non-treated, damaged control. Subjects left the lab and returned for measurements approximately 4 hours after treatment. On Day 1 after the 4 hour measurements were completed, the subjects rated any soothing effects they were able to perceive from the earlier application of the test products, a second application of the products was applied to the same sites and subjects rated the soothing effects they were able to perceive from the 2nd application of the test products.

On Days 2 and 3, the capacitance, conductance and TEWL measurements were repeated prior to the AM product application, followed by twice-daily treatment with the products to the same sites. All applications were done at the clinical studies location by a study technician.

On Day 4, the final measurements were taken and subjects again rated the soothing effects of the products they were able to perceive after 3 days of twice-daily application.

It is known that the use of petrolatum, by itself, can reduce TEWL by up to 98%. Thus, it is not surprising that the two comparison formulas, each comprising large quantities of petrolatum, performed well on the TEWL tests. What is surprising is that Example Formula #1, with no petrolatum, had results just as high on the TEWL testing. Further, it is surprising that Example Formula #1 provided better subjective hydration/moisturization than the GOLD BOND® product, and equal to the EUCERIN® product.

As is known in the industry, the TEWL test provides guidance with respect to how a product impacts the skin's ability to prevent water loss. However, the TEWL test only examines the overall quantity of water loss, not the cause of that water loss. Thus, it cannot distinguish between improvements in barrier properties due to the use of an occlusive barrier (such as petrolatum) and improvements due to skin actually being repaired.

To that end, Example Formula #1 was then used to assess the product efficacy in a pilot study with 5 diabetes mellitus (DM) patients. The product was applied to visibly cracked hands and heels over a 1 week time period. There, the results indicate that the formulation provides a significant reduction in discomfort associated with the cracked hands and heels with just one use. Further, and surprisingly, there is a 100% improvement in the skin, with DM patients indicating cracked hands and heels were repaired in just 1 week of application.

Certain embodiments comprise antioxidants capable of protecting living human cells from oxidative stress, as determined via a total phenolics assay utilizing Folin-Ciocalteu reagent. The composition showed a mild cellular antioxidant protection when tested twice in the Cellular Antioxidant Protection assay. The same composition also showed a significant decrease in ROS Reactive Oxygen Species (ROS) formation on human polymorphonuclear (PMN) cells. Other embodiments are able to reprogram human inflammatory cells to produce less free radicals, as determined via a Reactive Oxygen Species assay. Still other embodiments provided statistically significant support of skin cells during in-vitro scratch recovery tests.

One skilled in the art will recognize that embodiments of the present invention provide benefits beyond cracked hands and heels for DM patients, and will also provide benefit for other acute and chronic wound (skin injuries) and dermatological conditions related to topical skin barrier malfunction caused dryness, scaling, dehydration, cuts, scrapes and dermatitis, keratosis, acne, eczema, psoriasis, and any other diseases conditions that may cause temporary disruption to the skin, such as shingles, bed sores, ulcers, etc. Further, embodiments may also be applicable to non-human subjects, including pets (e.g., cats, dogs, etc.) and domesticated animals (e.g., horses, cows, sheep, etc.).

What is claimed is:

1. A wound dressing consisting essentially of urea, sacha inchi oil, and sea buckthorn.

2. The wound dressing of claim 1, wherein the weight ratio of the sacha inchi oil to the weight ratio of the sea buckthorn oil is from about 1:3 to about 3:1.

3. A method for treating compromised skin of a human, consisting essentially of the steps of:
   a) applying the wound dressing of claim 1 to at least a portion of compromised skin of the human;
   b) leaving the wound dressing on the skin of the human; and
   c) reapplying at least once a day to the skin of the human.

4. The method according to claim 3, wherein the wound dressing is applied to either a human having diabetes or a human having visible cracked skin, then reapplied such that the human receives at least two applications per day for at least 7 days.

5. The method according to claim 3, wherein the wound dressing is reapplied at least twice a day.

* * * * *